United States Patent
Dorsel et al.

(10) Patent No.: US 7,198,939 B2
(45) Date of Patent: Apr. 3, 2007

(54) APPARATUS FOR INTERROGATING AN ADDRESSABLE ARRAY

(75) Inventors: Andreas N. Dorsel, Menlo Park, CA (US); David A. King, Menlo Park, CA (US); Nicholas M. Sampas, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/080,641

(22) Filed: Feb. 21, 2002

(65) Prior Publication Data
US 2002/0132261 A1 Sep. 19, 2002

Related U.S. Application Data

(62) Division of application No. 09/493,958, filed on Jan. 28, 2000, now abandoned.

(51) Int. Cl.
C12M 1/36 (2006.01)
G01N 15/06 (2006.01)
B32B 5/02 (2006.01)

(52) U.S. Cl. ............... 435/283.1; 435/287.2; 422/68.1; 422/82.05; 422/82.08

(58) Field of Classification Search ........ 356/335, 356/336, 337, 338, 340, 343, 339, 73.1; 235/462.01, 235/462.41, 462.25, 462.11
See application file for complete search history.

(56) References Cited

U.S. PATENT DOCUMENTS

| 3,542,481 A | 11/1970 | Slomba |
| 3,704,951 A | 12/1972 | Chupp |
| 3,849,654 A | 11/1974 | Malvin |
| 3,850,525 A * | 11/1974 | Kaye ................. 356/73 |
| 4,052,621 A | 10/1977 | Haas |
| 4,088,407 A | 5/1978 | Schoeffel et al. |
| 4,188,542 A | 2/1980 | Hogg et al. |
| 4,188,543 A | 2/1980 | Brunsting et al. |
| 4,189,236 A | 2/1980 | Hogg et al. |
| 4,199,686 A | 4/1980 | Brunsting et al. |
| 4,222,743 A | 9/1980 | Wang |

(Continued)

FOREIGN PATENT DOCUMENTS

WO     WO 99/23492     5/1999

OTHER PUBLICATIONS

Website http://www.biodevice.com/SuperStrate.html., "SuperStrate", bioDevice partners, 2 pp. downloaded Jan. 27, 2000.

(Continued)

*Primary Examiner*—B J Forman

(57) ABSTRACT

A method and apparatus of interrogating an addressable array unit, which includes a substrate, a light reflecting layer on a front side of the substrate, and a plurality of features on a front side of the array. The method may include, for each of multiple features, illuminating the feature simultaneously with reflected and non-reflected interrogating light. A light emitted from respective features is detected. Either or both, constructive interference of interrogating light at the features, or constructive interference of light emitted from the features, can be obtained to allow lowering of light power from the source, enhanced signal, or reduced noise, or combinations of the foregoing. High depth discrimination may also be obtained without the need for a confocal detection system with conventional pinhole.

7 Claims, 4 Drawing Sheets

U.S. PATENT DOCUMENTS

| | | |
|---|---|---|
| 4,281,924 A | 8/1981 | Auer et al. |
| 4,341,993 A | 7/1982 | Brunsting et al. |
| 4,345,837 A | 8/1982 | Kallet |
| 4,348,107 A | 9/1982 | Leif |
| 4,533,246 A | 8/1985 | Braun |
| 4,549,807 A | 10/1985 | Hoffmaster |
| RE32,598 E | 2/1988 | White |
| 4,737,464 A | 4/1988 | McConnell et al. |
| 4,802,768 A | 2/1989 | Gifford et al. |
| 4,844,613 A | 7/1989 | Batchelder et al. |
| 4,847,508 A | 7/1989 | Kokubu |
| 4,854,705 A * | 8/1989 | Bachalo ............... 356/336 |
| 4,867,559 A | 9/1989 | Bach |
| 4,882,288 A | 11/1989 | North et al. |
| 4,907,883 A | 3/1990 | Allmon et al. |
| 4,931,384 A | 6/1990 | Layton et al. |
| 4,943,159 A | 7/1990 | Oetliker et al. |
| 5,006,716 A | 4/1991 | Hall |
| 5,018,866 A | 5/1991 | Osten |
| 5,026,159 A | 6/1991 | Allen et al. |
| 5,047,213 A | 9/1991 | Finlan et al. |
| 5,064,619 A | 11/1991 | Finlan |
| 5,118,608 A | 6/1992 | Layton et al. |
| 5,127,729 A | 7/1992 | Oetliker et al. |
| 5,173,434 A | 12/1992 | Morris et al. |
| 5,210,411 A | 5/1993 | Oshima et al. |
| 5,315,375 A | 5/1994 | Allen |
| 5,319,975 A | 6/1994 | Pederson et al. |
| 5,322,798 A | 6/1994 | Sadowski |
| 5,327,225 A | 7/1994 | Bender et al. |
| 5,374,563 A | 12/1994 | Maule |
| 5,478,755 A | 12/1995 | Attridge et al. |
| 5,484,571 A | 1/1996 | Pentoney, Jr. et al. |
| 5,611,998 A | 3/1997 | Aussenegg et al. |
| 5,631,734 A | 5/1997 | Stern et al. |
| 5,717,216 A | 2/1998 | McCoy et al. |
| 5,721,435 A | 2/1998 | Troll |
| 5,763,870 A | 6/1998 | Sadler et al. |
| 5,945,679 A * | 8/1999 | Dorsel et al. ............. 250/458.1 |
| 6,008,892 A | 12/1999 | Kain et al. |
| 6,025,601 A | 2/2000 | Trulson et al. |
| 6,118,532 A * | 9/2000 | Peters ................. 356/338 |
| 6,123,261 A * | 9/2000 | Roustaei ............... 235/462.01 |
| 6,177,990 B1 | 1/2001 | Kain et al. |
| 6,180,415 B1 * | 1/2001 | Schultz et al. ............. 436/518 |
| 6,215,894 B1 * | 4/2001 | Zeleny et al. ............. 382/133 |
| 6,232,072 B1 | 5/2001 | Fisher |
| 6,238,862 B1 | 5/2001 | McGall et al. |
| 6,406,849 B1 * | 6/2002 | Dorsel et al. ............ 435/6 |
| 6,476,382 B1 * | 11/2002 | Zhai et al. ............. 250/237 G |
| 6,826,422 B1 * | 11/2004 | Modell et al. ............. 600/407 |

OTHER PUBLICATIONS

Schalkhammer, Thomas, "Metal Nano Clusters as Transducers for Bioaffinity Interactions", Monatschefte fur Chemie, vol. 129, pp. 1067-1092, 1998.

Stratagene catalog, 1989, p. 39.

* cited by examiner

APPARATUS FOR INTERROGATING AN ADDRESSABLE ARRAY

This is a Divisional of application Ser. No. 09/493,958, filed on Jan. 28, 2000, now abandoned, the entire disclosure of which is incorporated herein by reference.

FIELD OF THE INVENTION

This invention relates to optical illumination and optical sensing of arrays, particularly biopolymer arrays such as DNA arrays, which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include features (sometimes referenced as spots or regions) of usually different sequence polynucleotides arranged in a predetermined configuration on a substrate. The array is "addressable" in that different features have different predetermined locations ("addresses") on a substrate carrying the array.

Biopolymer arrays can be fabricated using in situ synthesis methods or deposition of the previously obtained biopolymers. The in situ synthesis methods include those described in U.S. Pat. No. 5,449,754 for synthesizing peptide arrays, as well as WO 98/41531 and the references cited therein for synthesizing polynucleotides (specifically, DNA). In situ methods also include photolithographic techniques such as described, for example, in WO 91/07087, WO 92/10587, WO 92/10588, and U.S. Pat. No. 5,143,854. The deposition methods basically involve depositing biopolymers at predetermined locations on a substrate which are suitably activated such that the biopolymers can link thereto. Biopolymers of different sequence may be deposited at different feature locations on the substrate to yield the completed array. Washing or other additional steps may also be used. Procedures known in the art for deposition of polynucleotides, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of an ink jet type head to fire drops onto the substrate).

In array fabrication, the quantities of DNA available for the array are usually very small and expensive. Sample quantities available for testing are usually also very small and it is therefore desirable to simultaneously test the same sample against a large number of different probes on an array. These conditions require the manufacture and use of arrays with large numbers of very small, closely spaced features.

The arrays, when exposed to a sample, will exhibit a binding pattern. The array can be interrogated by observing this binding pattern by, for example, labeling all polynucleotide targets (for example, DNA) in the sample with a suitable label (such as a fluorescent compound), scanning an interrogating light across the array and accurately observing the fluorescent light (sometimes referenced as a "light signal" or "signal") from the different features of the array. Assuming that the different sequence polynucleotides were correctly deposited in accordance with the predetermined configuration, then the observed binding pattern will be indicative of the presence and/or concentration of one or more polynucleotide components of the sample. Peptide arrays can be used in a similar manner. Techniques for scanning arrays are described, for example, in U.S. Pat. No. 5,763,870 and U.S. Pat. No. 5,945,679. However, the light detected from respective features emitted in response to the interrogating light, may be other than fluorescence from a fluorescent label. For example, the detected light may be from fluorescence polarization, reflectance, or scattering, as described in U.S. Pat. No. 5,721,435.

Array scanners typically use a laser as an interrogating light source, which is scanned over the array features. Particularly in array scanners used for DNA sequencing or gene expression studies, a detector (typically a fluorescence detector) with a very high light sensitivity is normally desirable to achieve maximum signal-to-noise in detecting hybridized molecules. At present, photomultiplier tubes ("PMTs") are still the detectors of choice although charge coupled devices ("CCDs") can also be used. PMTs are typically used for temporally sequential scanning of array features, while CCDs permit scanning many features in parallel. Often a confocal detector system is used which to provide high depth discrimination and thereby reduce noise such as fluorescence of the substrate. However, this also results in capture of only a very small proportion of the emitted fluorescent light.

While detectors may be highly sensitive, the fluorescence detected may still be very weak, particularly where very little of a fluorescently labeled target is bound to a particular array feature. Weak signals may lead to errors in array interrogation and subsequent misinterpretation of results. Interrogating light power to a feature can be increased but this requires a more powerful source (typically a laser). Furthermore, increasing interrogating light power to a feature is not always an option, since fluorescent moieties rapidly become saturated such that an increase in interrogating light power does not increase signal, but may increase noise.

The present invention realizes that it would be desirable then, when possible without saturation, to provide a high interrogation light power at a feature without necessarily having to increase the output available from the interrogating light source. The present invention further realizes that it would be desirable to detect as much of the signal emitted from a feature as possible, without having to further increase interrogating light power, while maintaining detected noise at a low level.

SUMMARY OF THE INVENTION

The present invention then, provides a method for use with an addressable array of multiple features of different chemical moieties. The array is part of an array unit having a substrate, a light reflecting layer on a front side of the substrate, and the array features positioned forward of the light reflecting layer. The moieties may, for example, be polynucleotides (such as DNA or RNA) of different sequences for different features, or peptides of different amino acid sequence or secondary structure.

In one aspect of the method, a feature is illuminated simultaneously with interrogating light which is both reflected and non-reflected from the reflecting layer. This can be performed for each of the multiple features. That is, the reflected and non-reflected light falls simultaneously on a given feature at a given time, while each features is preferably, but not necessarily, illuminated individually in sequence by a light spot. A light signal emitted from respective features in response to the interrogating light, is detected.

The present invention also provides a method of interrogating an array of the type described, in which light emitted from respective features is detected. In this method the detected light is a combination of emitted light which is both reflected and non-reflected from the reflecting layer. The light may be emitted in response to an interrogating light (for example, by fluorescence) or otherwise (for example, chemiluminescence).

In an aspect of the present invention, the features may be illuminated simultaneously by constructively interfering reflected and non-reflected interrogating light (which may or may not have a large degree of coherence) with proper choice of interrogating light wavelength and spacer thickness. For example, the interrogating light wavelength, spacer layer thickness, and angle of illumination in this arrangement can be such that a standing wave is generated with the features at about an anti-node. In another aspect, the detected emitted signal can be a combination of constructively interfering reflected and non-reflected emitted signal. Either or both of these benefits can be obtained with proper choice of the emitted signal wavelength and bandwidth, spacer thickness, and a detection angle. For example, with the correct choice of the emitted signal wavelength and bandwidth, spacer thickness, and detection angle, the detected emitted signal may be at a maximum with other conditions remaining the same. Ideally, the reflected and non-reflected emitted signals will be coherent and in phase or close to it. For a given array which is interrogated in a given apparatus, generally the detection angle will be adjusted as required to obtain a maximum signal prior to interrogating the array. Note that throughout the present application, illumination and detection angles are measured with respect to a normal to the reflecting layer (at the point of reflection), unless in a specific instance a contrary indication is provided.

In a further aspect of the invention, the light emitted by the features may be of at least two wavelengths (each being emitted from the same or different features) each of which is preferably different from, an interrogating light wavelength. In this case, the light of different wavelengths emitted from respective features are detected at respective different detection angles. The spacer thickness, and each different emitted light wavelength and detection angle are such that each detected emitted light of different wavelength, is a combination of constructively interfering reflected and non-reflected emitted light.

In the present invention, when features emit light in response to an interrogating light (versus, for example, emitting light by chemiluminescence) the interrogating light may initially be directed from the front side. The interrogating light is preferably ("preferably", "may" and the like, implying not necessarily) monochromatic, and the features preferably emit a light of wavelength different from the interrogating light. In a preferred arrangement, the interrogating light is initially directed from the front side as a spot which is scanned across features to illuminate each in turn. Further, the emitted light may result from fluorescence of a fluorescent label at the features. In one arrangement, the features include corresponding moieties linked to the substrate, and the method additionally comprising, prior to illuminating the features, exposing the array to a sample such that the linked moieties of at least some of the features bind to respective moieties in the sample which sample moieties include the fluorescent label. Particularly, the linked moieties may be polynucleotides of respective different sequences hybridized with fluorescently labeled polynucleotides. Each detection angle may typically be from zero to up to less than ninety degrees.

The present invention further provides an addressable array of the types described above. The spacer layer may particularly be of a thickness such that the distance from the reflecting layer to the actual light emitting moiety of the features (such as the fluorescent labels mentioned above) is about ¼ the wavelength of the interrogating or emitted light (the wavelength being measured in the spacer layer). This construction can result in the features being at about the previously mentioned anti-node when the interrogating light is directed to the array perpendicular to the array surface. Since "light" includes infra-red to ultraviolet over a range of about 200 to 300 nm, and given that the moieties themselves will be relatively short, a typical spacer thickness may for example be between 50 nm to 750 nm thick, and more preferably between 50 nm to 150 nm thick, or some integral multiple within the foregoing ranges. There is also provided a kit of the present invention which may include such an array and instructions (whether machine or human readable) on a suitable medium (for example, disk or paper) that it is to be used with an interrogating light of indicated wavelength. An apparatus for interrogating an addressable array of multiple features of different moieties is also further provided. Such an apparatus includes a light source to provide the interrogating light, and a detector system to detect light signals emitted by respective features in response to the interrogating light, at multiple different detection angles. Note that multiple different angles of interrogating light (when used) and/or detection can be obtained by altering the angle of the interrogating light or the detector with respect to the array (for example, either the interrogating light or detector can be moved), or both. Alternatively, multiple interrogating light sources or multiple detectors can be provided, such that the different interrogating light and/or detection angles are obtained. The apparatus may also include a reader (which implies a suitable machine) to read a code carried by an array package, and a processor which causes the detector system to detect emitted light at a detection angle based on the read code.

The present invention further provides a computer program product for use in an apparatus of the present invention wherein the detection angle (or interrogating light wavelength) is adjustable. Such a computer program product includes a computer readable storage medium having a computer program stored thereon which, when loaded into a computer of the apparatus, causes it to adjust the detection angle (or interrogating light wavelength) based on an identification ("ID") read (preferably machine read) from an array package carrying the array (with the required information being retrieved from the read ID or from a local or remote database).

While the methods and apparatus may be described in connection with arrays of various moieties, such as polynucleotides or DNA, other moieties can include any other chemical moieties such as biopolymers. Also, while the detected light may particularly be fluorescent emissions in response to the interrogating light, other detected emitted light in response to the interrogating light can include polarization, reflectance, or scattering, signals.

The present invention then can provide any one or more of a number of FER advantages. For example, a higher interrogation light power can be provided at a feature without having to increase the output available from the interrogating light source, or the same interrogating light power can be obtained at the feature and the source output power lowered. Also, high detected signal can be obtained without having to further increase interrogating light power (and possibly risking saturation in certain situations), while maintaining detected noise at a low level. Combinations of the foregoing are also possible. By adjusting spacer layer thickness and detection angle for a given array the signal which can be detected can be maximized. By providing a reflecting layer, the detector also does not receive light emitted from the substrate, reducing the need for confocal detection and an auto-focus detector system while still providing high depth discrimination. Also, with constructive interference of reflected and non-reflected emitted light, such emitted light can be concentrated on or near the surface of a cone positioned with an apex at the features. This can simplify the ability to capture more of the emitted light.

BRIEF DESCRIPTION OF THE DRAWINGS

Embodiments of the invention will now be described with reference to the drawings, in which.

To facilitate understanding, the same reference numerals have been used, where practical, to designate similar elements that are common to the FIGS. Unless otherwise indicated, illustrated components are not necessarily shown in scale.

DETAILED DESCRIPTION OF THE INVENTION

Figure 1:
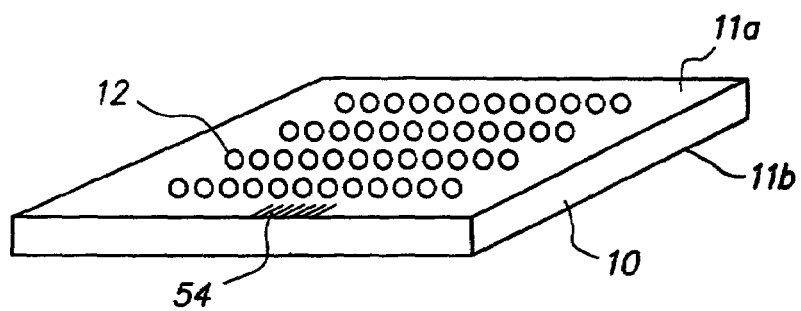
FIG. 1 is a perspective view of an array unit carrying a typical array of the present invention.

Throughout the present application, unless a contrary intention appears, the following terms refer to the indicated characteristics. A "biopolymer" is a polymer of one or more types of repeating units. Biopolymers are typically found in biological systems and particularly include peptides or polynucleotides, as well as such compounds composed of or containing amino acid or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as analogs (whether synthetic or naturally occurring) of such sub-units. For example, a "biopolymer" includes DNA (including cDNA), RNA, oligonucleotides, and PNA and other oligonucleotides as described in U.S. Pat. No. 5,948,902 and references cited therein (all of which are incorporated herein by reference), regardless of the source. An "oligonucleotide" generally refers to a polynucleotide of about 10 to 100 nucleotides (or other units) in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution). An "addressable array" includes any one or two dimensional arrangement of discrete regions (or "features") bearing particular moieties (for example, different polynucleotide sequences) associated with that region and positioned at particular predetermined locations on the substrate (each such location being an "address"). These regions may or may not be separated by intervening spaces.

By one item being "remote" from another, is referenced that the two items are at least in different buildings, and may be at least one mile, ten miles, or at least one hundred miles apart. An array "package" may be the array plus only a substrate on which the array is deposited, although the package may include other features (such as a housing). A "chamber" references an enclosed volume (although a chamber may be accessible through one or more ports). It will also be appreciated that throughout the present application, that words such as "top", "upper", and "lower" are used in a relative sense only. "Fluid" is used herein to reference a liquid. "Constructive interference", and "coherence", are defined below in connection with FIG. 4. Illumination, detection, and other angles are measured with reference to a normal to the reflecting layer unless in a specific case another reference is indicated. By "reflection" of light or similar terms, is referenced at least 10% of the incident light is reflected, and preferably at least 20%, 50%, 80% or at least 90% or 95%. Reference to a singular item, includes the possibility that there are plural of the same items present. All patents and other cited references are incorporated into this application by reference.

Figure 2:
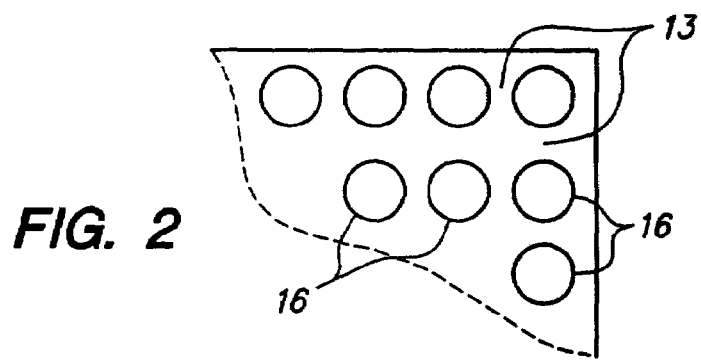
FIG. 2 is an enlarged view of a portion of FIG. 1 showing some of the array features more clearly.
Figure 3:
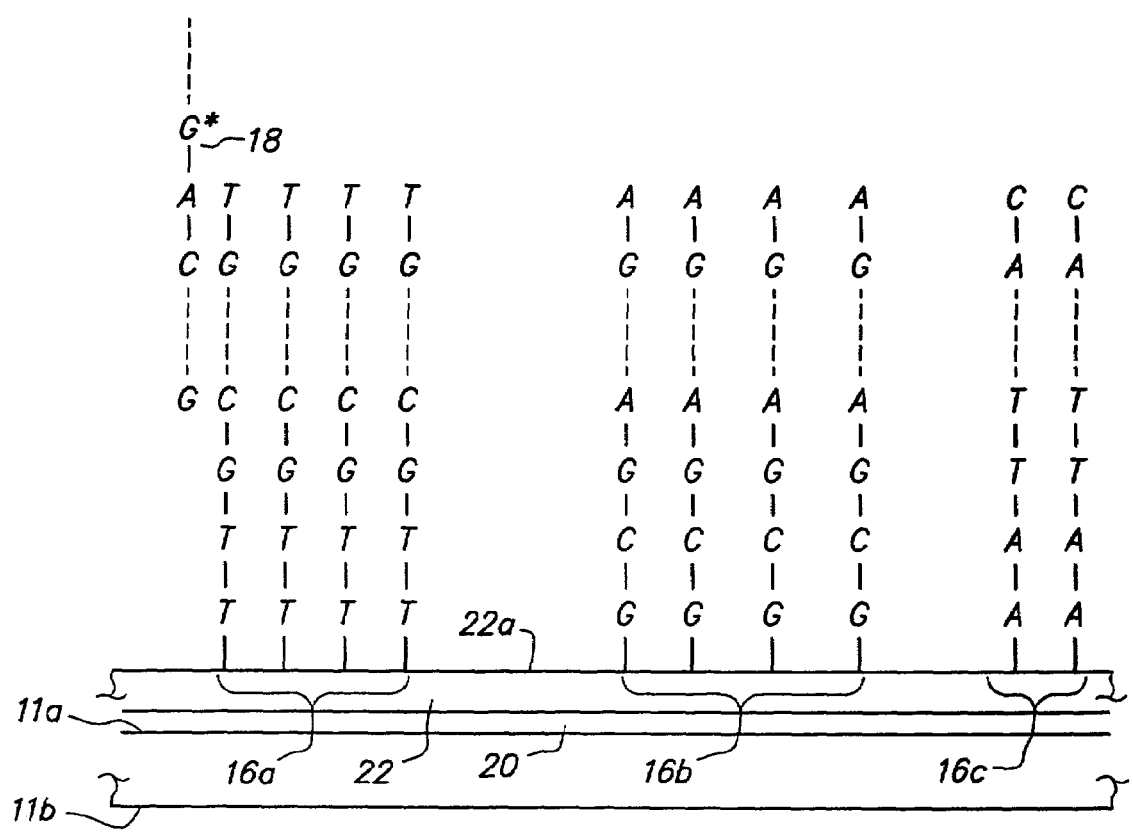
FIG. 3 is an enlarged cross-section of a portion of FIG. 2.

Referring first to FIGS. 1–3, the illustrated array unit includes a contiguous planar transparent substrate 10 carrying a light reflecting layer 20 of uniform thickness on a front side 11a of substrate 10. A transparent spacer layer 22 of uniform thickness is provided on a front side 20a of reflecting layer 20. Multiple features 16 are disposed across front side 20a of reflecting layer 20, and are separated by areas 13. Features 16 are disposed in a pattern which defines the array. A back surface 11b of substrate 10 does not carry any features. Substrate 10 may be of any shape although the remainder of the package of the present invention may need to be adapted accordingly. A typical array may contain at least ten features 16, or at least 100 features, at least 100,000 features, or more. All of the features 16 may be different, or some or all could be the same. Each feature carries a predetermined moiety or mixture of moieties which in the case of FIGS. 1–3 is a polynucleotide having a particular sequence. This is illustrated schematically in FIG. 3 where regions 16 are shown as carrying different polynucleotide sequences. Note that the polynucleotides may be linked indirectly to substrate 10 through suitable linker molecules (not shown), and that features 16 may exclude any metal atoms or particles to which biopolymers such as the polynucleotides are linked. As to the thickness of spacer layer, this should be selected as discussed below.

Arrays of FIGS. 1–3 can be manufactured by in situ or deposition methods as discussed above. In use, the array can be exposed to a sample such that a feature can detect a polynucleotide of a complementary sequence in the sample by hybridizing to it. One such hybridized complementary polynucleotide is illustrated as polynucleotide 18 on which the "*" indicates a label such as a fluorescent label. Use of arrays to detect particular moieties in a sample (such as target sequences) are well known.

The array unit of FIGS. 1–3 preferably includes an identification ("ID") 54 of the array. The identification 54 may be in the form of a bar code or some other machine readable code applied during the manufacture of array package 30. Identification 54 may itself contain instructions for a scanning apparatus that detection angle or interrogating light wavelength is to be adjusted to a certain value or values prior to scanning. These instructions are predetermined based on the spacer layer thickness, the emission wavelength from the fluorescent labels, and either of the interrogating light wavelength or detection angle. Alternatively, identification 54 may be simply a unique series of characters which is also stored in a local or remote database in association with the foregoing location information. Such a database may be established by the array manufacturer and made accessible to the user (or provided to them as data on a portable storage medium). Also, identification 54 may optionally just provide information on the array (for example, spacer layer 22 thickness) by either of the foregoing routes, for a scanner apparatus to calculate the detection angle to obtain maximum detected signal using this information and information obtained elsewhere (for example, fluorescent label emission wavelength input by a user).

It will be appreciated though, that other configurations of an array unit may be used. For example, an array unit may further include a housing with a closed chamber accessible through one or more normally closed valves (such as septa). The array unit of FIGS. 1–3 may be positioned within such package with the array facing into the chamber toward a transparent window through which interrogating light may be directed (if used) and emitted light detected.

The components of the array unit described above, may be made of any suitable material. For example, substrate 10 may be of transparent or non-transparent materials, which include, for flexible substrates: nylon, both modified and unmodified, nitrocellulose, polypropylene, and the like. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like). Reflecting layer 20 can be made of a metal, metal oxide, or other reflecting materials. The thickness of layer 20 is not critical provided it is sufficiently thick to efficiently reflect light of the wavelength of the interrogating or emitted light (for example, reflecting at least 60% of such light, or more preferably at least 80%, and more preferably at least 90% or 95%. Reflecting layer 20 can be deposited by known means (such as by chemical or vapor deposition techniques). Spacer layer 22 can be formed of fused silica or glass, for example, and can be deposited at the required thickness by known methods. Spacer layer 22 should be transparent and, for example, allow at least 70%, preferably at least 90%, and more preferably at least 90% or 95% of interrogating or emitted light to pass through its thickness. The materials from which substrate 10 and housing 34 (at least the portion facing toward the inside of chamber 36) may be fabricated should ideally themselves exhibit a low level of binding during hybridization or other events.

Figure 4:
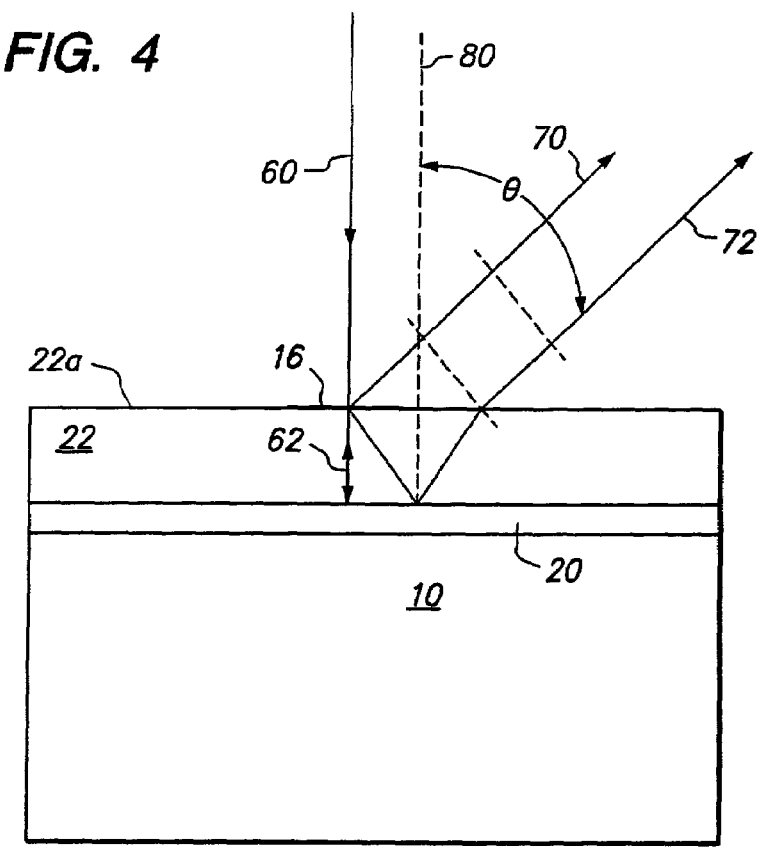
FIG. 4 illustrates a principle of operation of the present invention.

Referring to FIG. 4, a principle of operation of methods of the present invention is illustrated using an interrogating light beam 60 at a 0° illumination angle (sometimes referenced as angle "β"), and a detection angle "θ" with respect to the interrogating light beam which is greater than 0° but less than 90° (for example between 10° to 80°, or between 30° to 60°). As earlier mentioned, the illumination angle β is measured with respect to a normal to the feature 16 being illuminated (and in FIG. 4 is 0° since the illuminating beam is normal to the feature 16), while the detection angle θ is measured with respect to a normal 80 to the reflecting layer 20. At least in the Figure these normals are parallel. In particular, a feature 16 on substrate 10 of an array to be interrogated, is illuminated from the front side by preferably a coherent, monochromatic interrogating light spot provided by interrogating beam 60 (such as from a laser). Beam 60 passes through transparent spacer layer 22, and is reflected back as reflected beam 62 from reflecting layer 20. When the distance between a fluorescent label such as that on polynucleotide 18 and reflecting layer 20 is exactly the value of formula (I) (with λ being the wavelength of the interrogating light), then a standing wave with an anti-node (a maximal power value) will be present at the label. Thus, the feature 16 (specifically, the fluorescent label therein) will be illuminated with constructively interfering non-reflected light (beam 60) and reflected light (beam 62).

When labels on feature 16 fluoresce, emission is essentially in all directions. However, with an appropriate thickness of reflecting layer 22 discussed below, and wavelength of the emitted fluorescent light, when the detection angle θ is correctly chosen both emitted light reflected by reflecting layer (illustrated by beam 72) and non-reflected light (illustrated by beam 70) will constructively interfere and preferably will be at a maximum (where both are in phase). Thus, a detector positioned to receive beams 70 and 72 will receive light of greater power than would be received by it had the feature 16 been illuminated with the same power of interrogating light (including reflected and non-reflected) but with the reflecting layer 20 absent. Furthermore, since there is "constructive interference" as defined in this application, the detected power is greater than would be received from simple addition of two non-coherent beams of the same individual power. At this point it should also be appreciated that the appropriate detection angle θ allows a detector to be placed anywhere on a cone around feature 16 with a side having the angle φ (that is, beams 70, 72 are really part of cones). In this application it is assumed that beams 70 and 72 are plane waves with the normal to the beams' phase fronts indicated by the lines 70 and 72 drawn in FIG. 4. Both beams 70 and 72 impinge on a detector and the output signal of the detector will be proportional to the total incident intensity which is given by the square of the sum of the electric fields of beams 70 and 72. The total intensity will exhibit interference as a function of "d" the thickness of spacer layer 20 and detection angle θ. It will be apparent that the following discussion and theory can be modified to include non-uniform thickness of the spacer layer 20.

In general, for a maximum intensity in detected signal the relationship between angle "θ" and the thickness "d" of spacer layer 20 is given by:

$$d = \frac{m \cdot \lambda}{\sqrt{2n_2(1-X^2)}} \quad (1)$$

where:

$$X = \frac{n_1}{n_2}\sin\theta \quad (2)$$

and that d also satisfies the following formula:

$$d < \frac{c}{2 \cdot \Delta v \cdot n_2 \cdot \cos\theta_t} \quad (3)$$

where m is any integer (such as any integer between 1 and 11, preferably 3 or 1); $\lambda$ is the wavelength of the light in vacuum; $\Delta v$ is the bandwidth of the emitted light; $n_1$ is the index of refraction from the surrounding media (usually air); and $n_2$ is the index of refraction of the spacer layer. For an elastic process, such as scattering of light from particles, $\Delta v$ is the linewidth of the incident light source. For an inelastic process, such as fluorescence detection, $\Delta v$ is the Lorentzian spectral broadening (in Hz) of the light of the fluorophores in medium 1, and c is the speed of light. It will be apparent that the above discussion and equations can be extended to non-plane wave situations.

"Constructive interference" at the detector means that the detected light intensity (or power) from multiple paths is greater than the sum of those intensities if each path were detected separately and the resulting signals simply added. In essence, the relation (3) states that the light emitted by the label is sufficiently coherent (simply referenced as "coherent" light herein) to interfere constructively when the optical pathlength difference between the two light paths indicated in FIG. 4 is shorter than the coherence length of the emitted light, for example by the fluorophore (see R. Loudon, *Quantum theory of light*, Clarendon Press, Oxford, 1990, p92), where the coherence length is $c/\Delta v$. For the case of constructive interference of the emitted light, if the broadening of the fluorophore is 40 nm and the center wavelength of the fluorescence is a wavelength of 640 nm, then Equation 3 implies that the thickness of the spacer layer must be less than about 5 microns for a substantial constructive interference to be observed.

The same relationships in (1) through (3) above hold true for the interrogating light except that in each case θ is replaced with the corresponding angle of illumination, β (measured, as usual, with respect to the normal to the reflecting layer 20), and $\Delta v$ is the bandwidth of the illuminating light. In particular, the light beam 62 in FIG. 4 is the incident light beam 60 (sometimes referenced as the non-reflected beam) after it reflects from the reflecting layer 20. Feature 16 then, is simultaneously illuminated with the non-reflected light beam 60 and the reflected light beam, 62. "Constructive interference" occurs at feature 16 when the light intensity at feature 16 from the combined beams taking multiple paths 60 and 62 is greater than the sum of those intensities (averaged over time) if each path is considered separately. The non-reflected beam 60 illuminating the label 16 constructively interferes with reflected beam 62, when the coherence length of light beam 60 is greater than the optical path difference between light beams 60 and 62. The coherence length of light beam 60 is $c/\Delta v$ where c is the speed of light and $\Delta v$ is the bandwidth of the light source.

Thus, the relationship between the angle β of the incident beam 60 in FIG. 4 and the thickness of the spacer layer is given by:

$$d = \frac{m \cdot \lambda}{\sqrt{2n_2(1-y^2)}} \quad 1(a)$$

where:

$$y = \frac{n_1}{n_2}\sin\beta$$

Where it is desired to obtain maximum interrogation light power at a feature 16 for a given illumination angle, d should ideally be chosen so that the feature 16 is positioned at about an anti-node. By a feature being at "about" at an anti-node, is referenced within a distance of less than 25% of a wavelength of an anti-node, and more preferably within 10% or 5% of a wavelength of an anti-node.

Similarly, where it is desired to obtain maximum detected signal, an appropriate d should be chosen. It should also be noted that where the light emitting moiety will be provided at some point after fabrication of the array, such as by target polynucleotide hybridizing with polynucleotide probes, the typical expected distance from the front side 22a of spacer layer to the light emitting moiety (such as a fluorescent label), should be allowed for. That is, in the perpendicular interrogating light or detection angle cases referenced, the thickness of the spacer layer will be about the value provided by formula (I) minus the typical expected distance from the front of the spacer layer to the light emitting moiety. Typically, the foregoing expected distance is relatively small. However, the net result will often imply, for polynucleotide arrays used to detect typical polynucleotide targets, a spacer layer thickness of between 50 nm to 200 nm, and more preferably between 80 nm to 150 nm, or some integral multiple of the foregoing.

It will be appreciated that a standing wave generated from the interrogating light using the above arrangement can be used to either increase emitted signal from the features (in the fluorescent label situation, at least when the label is not already saturated) by virtue of increased illumination power at the features, or to obtain the same emitted light signal with less laser power. Using less laser power reduces background noise due, for example, to water Raman radiation in the operation of the scanning apparatus, while still maintaining high interrogating light power at the features. On the other hand, with the presence of a standing wave and the features correctly positioned at or about the anti-node, the increase in interrogating light power at the features can be up to fourfold (although any degree of power increase from constructive interference is advantageous, for example even at least a 1.5 or at least a 2 times increase). For emitted light, the interference pattern caused by the presence of reflecting layer 20 effectively changes the angular distribution of emitted light so that more light falls into a cone of collection, and less misses it. Here too, the highest achievable improvement with reflecting layer 20 is a detected emitted power four times that without reflecting layer 20 (and assuming that interrogating light power at the features 16 is maintained constant)(again, any degree of increase from constructive interference will be advantageous, for example even at least a 1.5 or at least a 2 times increase). Since reflecting layer 20 can provide both effects simultaneously, an increase of detected signal of up to almost 16 times is theoretically possible.

Note that the cone of collection is a surface of a cone and a region on either side thereof, which cone has an apex at the array. The size of the region on either side of the conical surface will vary depending upon factors discussed above, such as coherency of interrogating or emitted light, thickness of the spacer layer, the wavelength profile of the emitted light band (i.e. the width of a curve of power versus wavelength for the emitted light). For example, a cone of detection can be defined as being a given angle plus/minus the angle on either side thereof where the light power falls to 50% (or alternatively to 30 or 20%). For example, the cone of detection may be the detection angle plus/minus no more than 10°, and preferably no more than 5°, 2°, or 1° (such that the cone of detection has a corresponding thickness of no more than 20°, 10°, 4° or 2°). It will also be appreciated that detectors do not receive light from the substrate and therefore as a result, it is not essential to provide a conventional confocal detection system with a pinhole arrangement to enhance depth discrimination.

Figure 5:
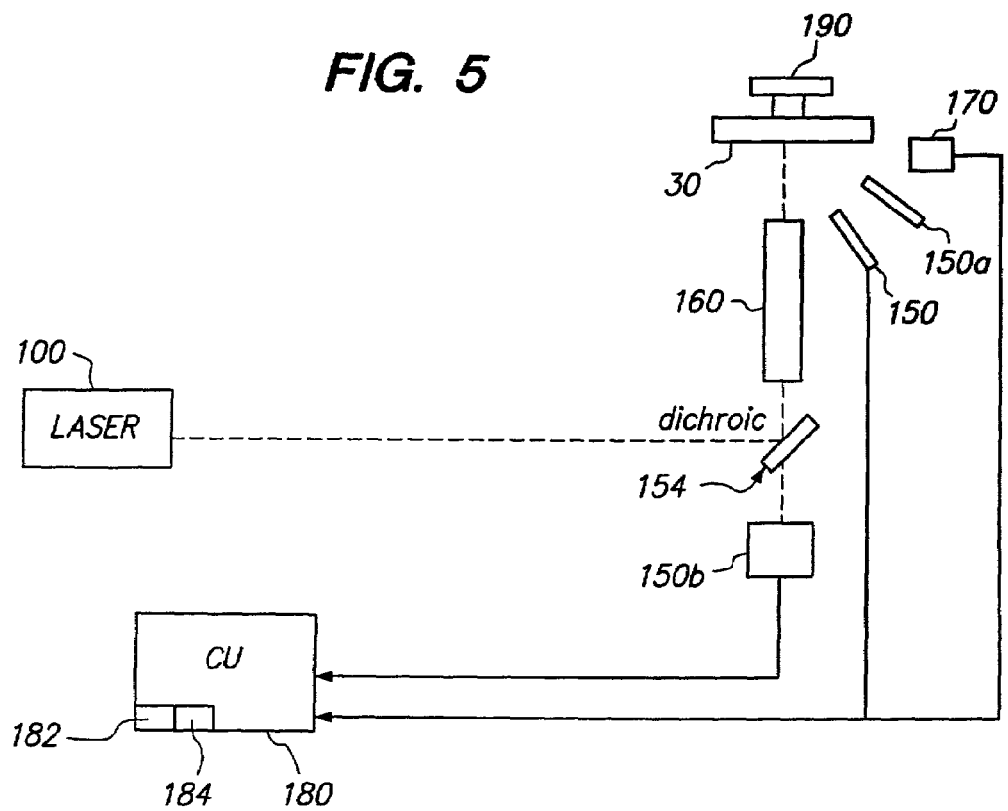
FIG. 5 illustrates an apparatus of the present invention.

Referring now to FIG. 5, an apparatus of the present invention (which may be generally referenced as an array "scanner") is illustrated with an array package 30 mounted therein. A light system provides a coherent monochromatic light from a laser 100 which is reflected off a dichroic beamsplitter 154 and focused onto the array of array package 30 using optical components in beam focuser/scanner 160. Light emitted from features 16 in response to the, interrogating light, for example by fluorescence, is imaged by a detector 150. Suitable optical components (not shown) may be used between the array package and detector 150 (such as lenses, pinholes, filters, fibers, and the like) and the detector 150 may be of various different types (e.g. a photo-multiplier tube (PMT) or a CCD or an avalanche photodiode (APD), CMOS array). Detector 150 is movable by a suitable transporter (not shown) into various detection angles (an alternative detection angle being illustrated by the position 150a in FIG. 5). Alternatively, the detector can be fixed at a detection angle of about 0°. In such a case, the detector can be positioned as illustrated at 150b and use the same optics in focuser/scanner 160, with detected light passing through dichroic beamsplitter 154 and onto the detector 150b. The angle of detection in this (or other) configuration can be altered by constructing transporter 190 to rotate package 30. However, rotating package 30 is less desirable in that it does not allow the detection angle to be controlled independently of the illumination angle.

A scanning system causes an interrogating light spot formed from laser 100 to be scanned across multiple sites on an array package 30 received in the apparatus, which sites include at least the multiple features 16 of the array. In particular the scanning system is typically a line by line scanner, scanning the interrogating light spot sequentially across features 16 of a row of features, then moving ("transitioning") the interrogating light to begin scanning a next row, scanning across that next row, and repeating the foregoing procedure row after row. The scanning system can be a suitable mechanism within beam focuser/scanner 160 which moves the interrogating light across a stationary array package 30, or can be a transporter 190 which moves array package 30 in relation to a stationary interrogating light beam, or may be a combination of the foregoing (for example, with beam focuser/scanner 160 scanning the interrogating light spot across a row of features 16 of the array, and with transporter 190 moving the array one row at a time such that beam focuser/scanner 160 can scan successive rows of features 16). Preferably the illumination angle is 0° for at least one location on the array (typically about the center of the array) with illumination angles for features ranging over +/− about 20°, and more preferably no more than +/− about 10° or even no more than +/−5° due to the scanning mechanism.

The apparatus of FIG. 5 may further include a reader 170 which reads identification 54. When identification 54 is in the form of a bar code, reader 170 may be a suitable bar code reader. A system controller 180 of the apparatus is connected to receive signals emitted in response to the interrogating light from emitted signal detector 130, as well as signals indicating a read identification from reader 170, and controls the transporter to adjust the detection angle of detector 150 based on the read identification (and may also control focuser/scanner 160 based on such read identification). Controller 180 may also analyze, store, and/or output data relating to emitted signals received from detector 130 in a known manner. Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 54). Controller 180 is suitably programmed to execute all of the steps required by it during operation of the apparatus, as discussed further below. Alternatively, controller 180 may be any hardware or hardware/software combination which can execute those steps.

In one mode of operation, the array in package 30 is typically first exposed to a liquid sample introduced into the chamber through one of the septa 42, 50. The array may then be washed and scanned with a liquid (such as a buffer solution) present in the chamber and in contact with the array, or it may be dried following washing. Referring in particular to FIG. 5 following a given array package 30 being mounted in the apparatus, reader 170 automatically (or upon operator command) reads array ID 54. Controller 180 can then use this ID 54 to retrieve information on one or more detection angles (or less preferably, interrogating light wavelength). Such information may be retrieved directly from the contents of ID 54 when ID 54 contains such information. Alternatively, ID 54 may be used to retrieve such information from a database containing the ID in association with such information. Such a database may be a local database accessible by controller 180, such as may be contained in a portable storage medium in drive 182 which is associated with package 30, such as by physical association with package 30 (for example, they were contained in the same package when received by the user, or are cross-referenced to another by a suitable identification), or may be a remote database accessible by controller 180 through communication module 184 and a suitable communication channel (not shown).

The transporter for detector 150 then positions detector 150 at the correct detection angle based on the information obtained from ID 54. As mentioned, this is preferably done by moving detector 150 with respect to package 30, but could be done by rotating package 30 although this would also then change the illumination angle. The interrogating laser light spot is then scanned across the array by focuser/scanner 160 to illuminate each of the multiple array features 16 in the manner described above. Constructive interference of reflected and non-reflected interrogating light will be obtained as described above particularly in connection with FIG. 4, with most or all features being at about an anti-node. Light emitted from respective features 16 in response to the interrogating laser light is detected, and the resulting emitted fluorescent light detected at detector 150. Such light should be constructively interfering reflected and non-reflected emitted light with the correct choice of spacer layer 22 thickness, emitted light wavelength, and detection angle, as discussed above. If more than one wavelength of emitted light is to be detected (as, for example, when different targets in the sample are labeled with labels which fluoresce at respective different wavelengths which are also different from the interrogating light wavelength), the foregoing process can be repeated with detector 150 moved to a different detection angle such as illustrated by position 150*a*. This movement and the value of the second detection angle can also be determined based on ID 54 in a similar manner as for the first detection angle. Alternatively, a second detector can be provided at position 150*a* and both wavelengths of emitted light detected simultaneously.

It will also be appreciated that controller 180 can determine, based on information obtained in any manner from ID 54 and known parameters of the scanner apparatus (such as interrogating light wavelength or possible detection angles of one or more detectors 150), whether a particular array package will not provide optimal results (such as maximum detected signal, or maximum interrogation light power at the array features) when scanned in the array apparatus in which it was mounted. An operator can be alerted to this fact through a suitable operator interface (not shown) which includes a suitable display (such as a CRT or LCD display).

Figure 6:
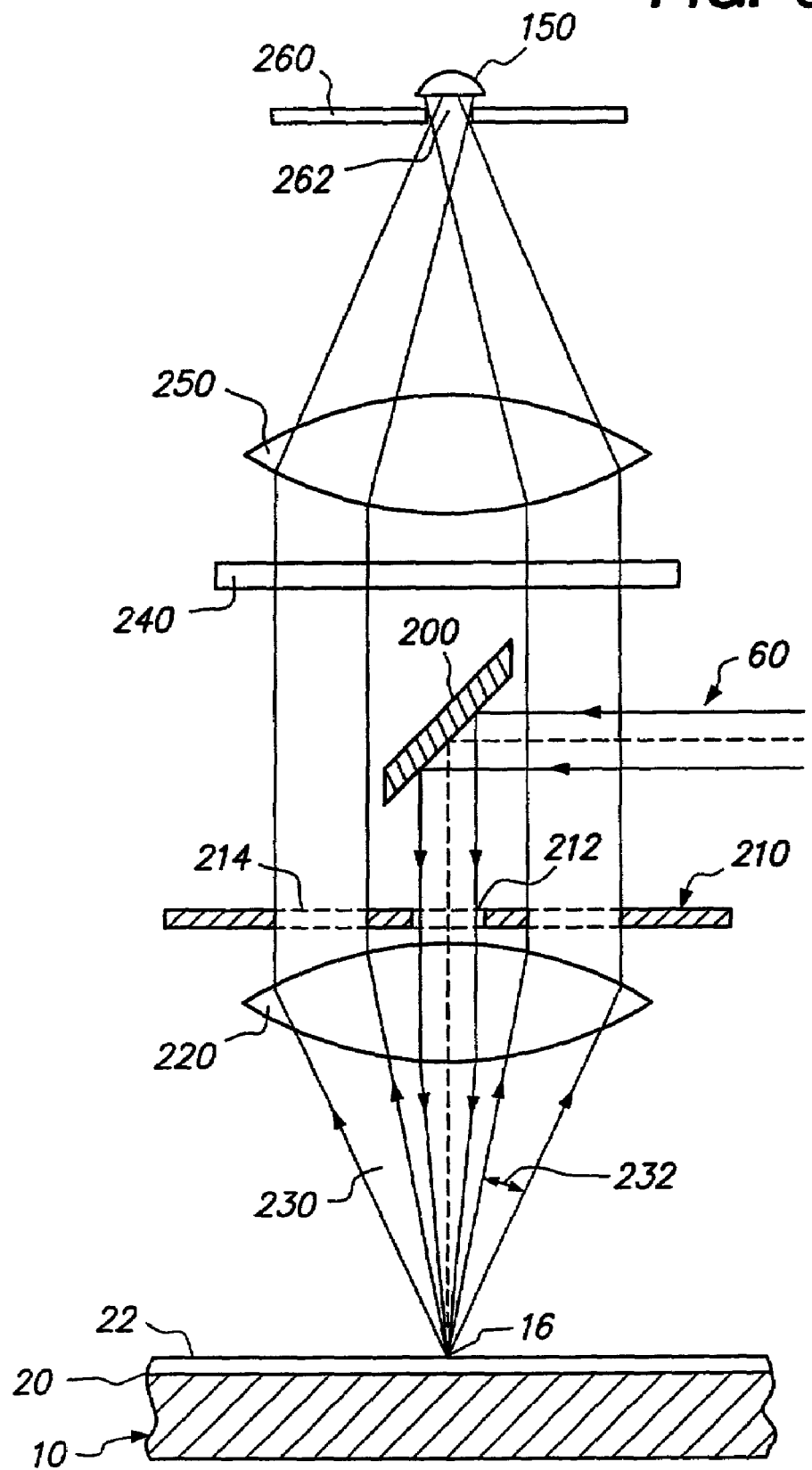
FIG. 6 illustrates in more detail a detection system of an apparatus of the present invention, which enables collection of most of the light of a single wavelength emitted from features.

While an apparatus such as that of FIG. 5 can be used, much of the light emitted in one or more cones for different emitted wavelengths, as discussed above, would not be collected by such an apparatus. More of such light can be collect if the detector system can collect light at multiple different positions around one or more of the cones, each with their apex at a array seated in the apparatus. One way of accomplishing this is to provide more detectors around the surface of cones on which detectors 150 and 150*a* lie. However, a more preferred way is to collect light from such cones simultaneously. FIG. 6 illustrates one such detection system for a single cone. In this configuration interrogating laser light beam 60 is reflected from mirror 200 through a central circular first aperture 212 in plate 210, then through objective lens 220 and onto a feature to be illuminated. Other features can be illuminated by scanning beam 60 across the array as previously discussed. Light emitted in response at a first cone 230 which subtends an angle 232, then passes through annular second aperture 214, emission filter 240 (which filters out light of the interrogating light wavelengths), and detection lens 250 which focuses the light through a pinhole or aperture 262 in plate 260 and onto detector 150.

Figure 7:
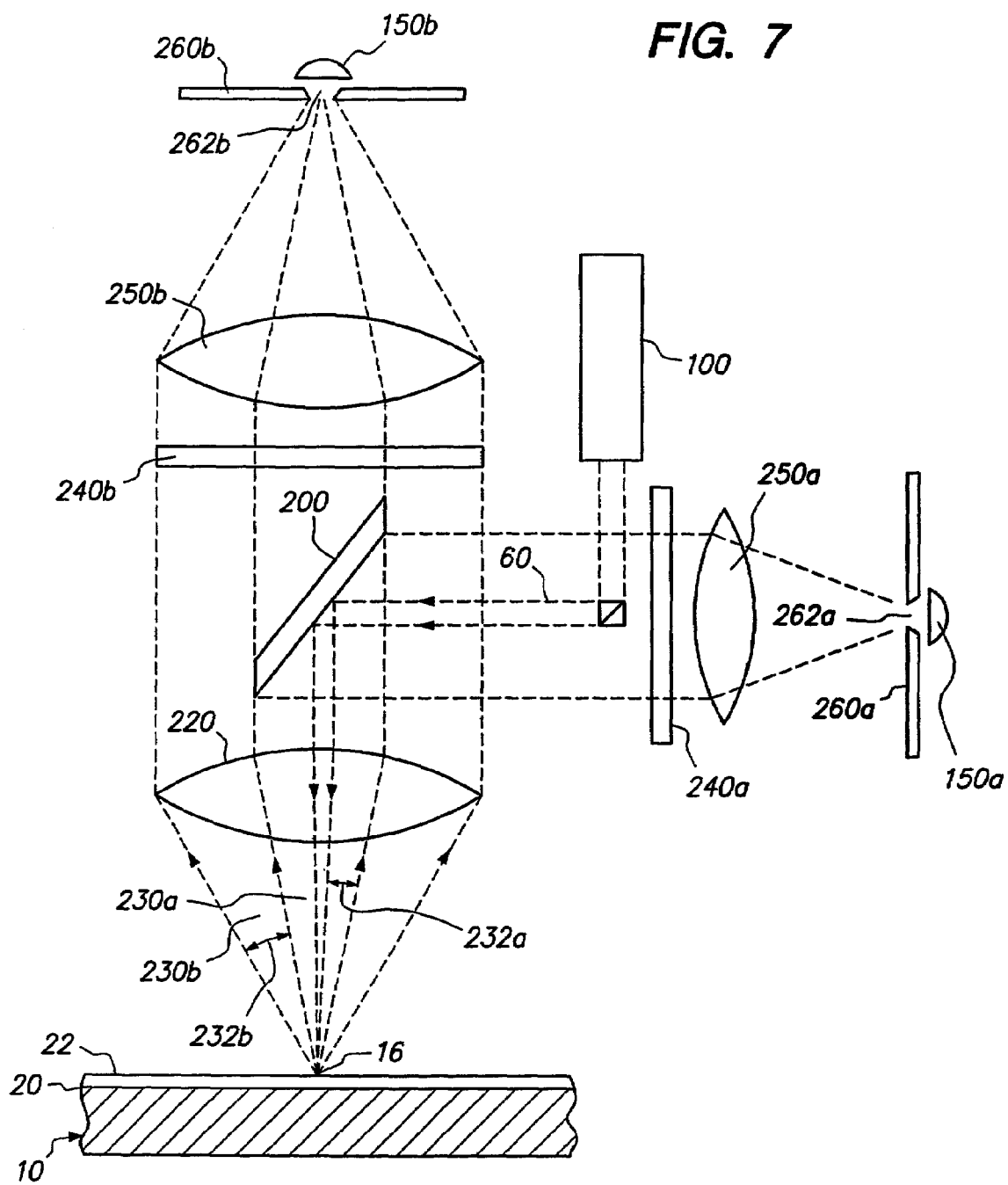
FIG. 7 is similar to FIG. 6 but illustrates a detection system which enable collection of most of the light of two different wavelengths emitted from features.

A similar detector system configuration as in FIG. 6, but for emitted light of two different wavelengths, is illustrated in FIG. 7. Interrogating laser light beam is again reflected of mirror 200 but this time directly through lens 220 onto an array feature 16. A first cone of detection 230*a* subtending angle 232*a*, is then collected by lens 220 and directed by mirror 200 through filter 240*a*, and lens 250*a* which focuses the light through a pinhole or aperture 262*a* in plate 260*a* and onto detector 150*a*. Similarly, a second cone of detection 230*b* subtending angle 232*b*, is then collected by lens 220 and directed by it through filter 240*b*, and lens 250*b* which focuses the light through a pinhole or aperture 262*b* in plate 260*b* and onto detector 150*b*. Filters 240*a* and 240*b* are designed to pass only light around the wavelengths which are to be detected in respective detection cones 230*a*, 230*b*. This eliminates detectors 150*a* and 150*b* detecting interrogating light 60 or other stray light.

Note that a variety of geometries of the features 16 may be constructed other than the organized rows and columns of the array of FIGS. 1–3. For example, features 16 can be arranged in a series of curvilinear rows across the substrate surface (for example, a series of concentric circles or semi-circles of spots), and the like. Even irregular arrangements of features 16 can be used, at least when some means is provided such that during their use the locations of regions of particular characteristics can be determined (for example, a map of the regions is provided to the end user with the array). Furthermore, substrate 10 could carry more than one array 12, arranged in any desired configuration on substrate 10. While substrate 10 is planar and rectangular in form, other shapes could be used with housing 34 being adjusted accordingly. In many embodiments, substrate 10 will be shaped generally as a planar, rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used. Less preferably, substrate 10 could have three-dimensional shape with irregularities in first surface 11*a*. In any event, the dimensions of housing 34 may be adjusted accordingly.

The apparatus of FIGS. 5–7 can be constructed accordingly to scan array packages of the described structure.

Various modifications to the particular embodiments described above are, of course, possible. Accordingly, the present invention is not limited to the particular embodiments described in detail above.

What is claimed is:

1. An apparatus for interrogating an addressable array of multiple features of different biopolymenc moieties, comprising:
    (a) an adjustable detection angle detector system comprising more than one detector each of which is aligned with an emission filter that filters out light of an interrogating wavelength such that each detector of the detection system detects light of different wavelengths at respective different detection angles with an optical axis aligned at each detection angle, wherein said system is configured for positioning at least one of said more than one detectors at a site for receiving a constructively interfering emission from an array having a reflective coating, wherein said system is further configured for determining said position for receiving a constructively interfering emission; and (b) a processor programmed to receive signals from the detector system and correlate the received signals with respective biopolymeric features of the array.

2. An apparatus according to claim 1 additionally comprising a light source to provide an interrogating light in response to which the features emit the light of different wavelengths.

3. An apparatus according to claim 2 wherein the light source produces a spot of light at the array, the apparatus additionally comprising a scanning system which scans the interrogating light spot across the array.

4. An apparatus according to claim 1 additionally comprising a reader to read a code carried by an array unit, and a processor which causes the detector system to detect emitted light at a detection angle based on the read code.

5. An apparatus according to claim 1 wherein said apparatus further includes an addressable array of multiple features of different biopolymeric moieties and a reflective coating.

6. An apparatus according to claim 5, wherein said array is forward of said reflective coating.

7. An apparatus according to claim 2, wherein said interrogating light source is configured for being adjusted in a manner sufficient to constructively illuminate a feature with both reflected and non-reflected light.

* * * * *